United States Patent [19]
Holt

[11] Patent Number: 5,605,619
[45] Date of Patent: Feb. 25, 1997

[54] DESULPHURIZATION TREATMENT

[75] Inventor: Andrew Holt, Fulwood, Great Britain

[73] Assignee: Dytech Corporation, Sheffield, Great Britain

[21] Appl. No.: 215,992

[22] Filed: Mar. 22, 1994

[30] Foreign Application Priority Data

Oct. 3, 1991 [GB] United Kingdom ............... 9120973

[51] Int. Cl.$^6$ ................................... C10G 25/05
[52] U.S. Cl. ............ 208/213; 423/230; 208/208 R; 208/217
[58] Field of Search ................. 208/249, 217; 423/230

[56] References Cited

U.S. PATENT DOCUMENTS

| | | | |
|---|---|---|---|
| 2,927,063 | 3/1960 | Batchelor et al. | 202/31 |
| 2,950,229 | 8/1960 | Batchelor et al. | 202/31 |
| 3,492,083 | 1/1970 | Lowicki et al. | 23/2 |
| 3,723,598 | 3/1973 | Spedden et al. | 423/244 |
| 3,761,570 | 9/1973 | Lowicki et al. | 423/225 |
| 3,945,914 | 3/1976 | Yoo et al. | 208/208 R |
| 3,983,030 | 9/1976 | Rosynek et al. | 208/208 R |
| 4,045,331 | 8/1977 | Ward | 208/213 |
| 4,120,865 | 10/1978 | Ward | 208/249 |
| 4,132,631 | 1/1979 | Nametkin et al. | 208/249 |
| 4,155,835 | 5/1979 | Antal | 208/212 |
| 4,329,220 | 5/1982 | Nelson | 208/89 |
| 4,593,148 | 6/1986 | Johnson et al. | 208/212 |
| 4,888,157 | 12/1989 | Carnell et al. | 423/230 |

*Primary Examiner*—Helane Myers
*Attorney, Agent, or Firm*—Caesar, Rivise, Bernstein, Cohen, and Pokotilow, Ltd.

[57] ABSTRACT

A manganese derivative preferably with a zinc derivative and/or a promoter is used to reduce the content of the sulphur content in a hydrocarbon stream especially at low temperature.

5 Claims, No Drawings

DESULPHURIZATION TREATMENT

The invention relates to desulphurisation treatment and in particular to the desulphurisation treatment of hydrocarbon streams (liquid or gas or both) by the partial or complete removal of sulphur compounds, e.g. hydrogen sulphide, low molecular weight mercaptans, or the like therefrom. In one aspect the invention provides a method of reducing the content of a sulphur compound in a hydrocarbon stream, the method comprising reacting the stream with a derivative of manganese for sufficient time to reduce the content of the sulphur compound characterised in that the reaction is carried out at a temperature from about ambient up to about 150° C.

Preferably the temperature is substantially ambient.

Preferably the manganese derivative is the oxide, hydroxide and/or carbonate, or the like.

The invention is based on the novel realisation that manganese dioxide or other derivative is an efficient agent for the removal of sulphur compounds at low temperature. The agent may be used neat or it may be included in other agents, e.g. mixtures based on promoted calcium derivatives, in major or minor proportions.

Preferably there is present a promoter selected from Groups IA, IB, IIA, VA and VIII of the Periodic Table, examples including potassium, sodium, iron, cobalt, nickel, copper, tin, bismuth, and specifically potassium hydroxide and nickel hydroxide and sodium hydroxide.

In a preferred feature, a zinc derivative, such as the oxide, hydroxide and/or carbonate, is present.

The sulphur compound to be removed may be hydrogen sulphide gas or a low molecular weight mercaptan such as propyl mercaptan. The hydrocarbon stream may be liquid or gas or both, examples being natural gas, town gas, synthesis gas, industrial waste gas, coke oven gas, coal gas, liquid or gas from a petroleum plant or oil refinery.

In yet another aspect the invention provides for use in the method a composition comprising bonded granules of a derivative of manganese optionally with a derivative of zinc. The bonding agent may be a cement, alumina or a clay, silica, organic resin; or the like.

It is believed that the use of a promoter in association with a manganese derivative is novel even when used at higher temperature.

In another aspect therefore the invention provides a method of reducing the content of a sulphur compound in a hydrocarbon stream, the method comprising reacting the stream with a derivative of manganese and a promoter selected from Groups IA, IB, IIA, VA and VIII of the Periodic Table for sufficient time to reduce the content of the sulphur compound.

The temperatures may be any of those used customarily.

In order that the invention may be well understood it will now be described by way of illustration with reference to the following examples.

EXAMPLES I

Zinc oxide powder (50 g) and manganese dioxide (50 g) and calcium aluminate cement (5 g) were dry mixed for 15 minutes. Water was added to the mix in sufficient quantity to form granules which were shaped to be of 3 mm mean diameter. These were dried at 150° C. for 5 hours.

EXAMPLE II

The method of Example I was repeated adding nickel hydroxide powder (3%) to the dry mix and potassium hydroxide (5%) to the water.

EXAMPLE III

The ability of different materials specified in the Table was tested by keeping them in a closed vessel containing hydrogen sulphide gas at 15° C. for 24 hours. The manganese dioxide was obtained from two sources, identified as (a) and (b). The uptake of the gas was determined by the increase in weight. The results are also shown in the Table from which it is clear that manganese dioxide is an efficient agent for removing the gas and that this effect may be improved by adding zinc carbonate or zinc oxide or a promotor.

TABLE

| Material | 1 | 2 | 3 | 4 | 5 | 6 | 7 | 8 | 9 | 10 |
|---|---|---|---|---|---|---|---|---|---|---|
| $MnO_2$(b) | | | 10 | 9 | 7 | 5 | 5 | | | |
| $MnO_2$(a) | | | | | | | | 10 | 5 | 1 |
| ZnO | 10 | | | | 2 | | | | 5 | 8 |
| $ZnCO_3$ | | 10 | | | | | 5 | | | |
| KOH | | | | | 2 | 1 | | | 0.5 | 1 |
| $Ni(OH)_2$ | | | | | | | | | 0.3 | |
| % increase in weight | 4.2 | 8.5 | 22.1 | 24.0 | 20.0 | 16.0 | 20.1 | 12.0 | 18.7 | 8.0 |

I claim:

1. A method of reducing the content of a sulphur compound in a hydrocarbon stream, the method comprising reacting the stream with bonded granules of a manganese-containing compound and a promoter, said promoter being nickel hydroxide, whereby the bonded granules take up an increased amount of the sulphur compound.

2. A method according to claim 1, wherein the reaction temperature is substantially ambient.

3. A method according to claim 1 or 2, wherein the manganese-containing compound is a manganese oxide, manganese dioxide, manganese hydroxide and/or manganese carbonate.

4. A method according to claim 1, including at least one zinc-containing compound selected from the group consisting of zinc oxide, zinc hydroxide and zinc carbonate, with the manganese-containing compound.

5. A method according to claim 1, wherein the sulphur compound to be removed is hydrogen sulphide gas or a low molecular weight mercaptan from a hydrocarbon stream which is selected from the group consisting of natural gas, town gas, synthesis gas, industrial waste gas, coke oven gas, coal gas, and liquid or gas from a petroleum plant or oil refinery.

* * * * *